United States Patent [19]

Alicot

[11] Patent Number: 4,647,669

[45] Date of Patent: Mar. 3, 1987

[54] PROCESS FOR THE PURIFICATION OF MERCAPTOBENZOTHIZAOLE

[75] Inventor: Michel Alicot, La Barthe de Neste, France

[73] Assignee: Manufacture Landaise de Produits Chimiques, France

[21] Appl. No.: 745,397

[22] Filed: Jun. 14, 1985

[30] Foreign Application Priority Data

Jun. 15, 1984 [FR] France .................. 84 09448

[51] Int. Cl.$^4$ .................................. C07D 277/72
[52] U.S. Cl. ................................................ 548/177
[58] Field of Search .......................... 548/177, 176

[56] References Cited

U.S. PATENT DOCUMENTS

| | | | |
|---|---|---|---|
| 1,631,871 | 6/1927 | Kelly | 548/177 |
| 1,712,968 | 5/1929 | Roberts et al. | 548/177 |
| 1,960,205 | 5/1934 | Dunbrook | 548/177 |
| 2,090,233 | 8/1937 | Roberts | 548/177 |
| 2,658,864 | 11/1953 | Ebel | 548/177 |
| 2,730,528 | 1/1956 | Weyker et al. | 548/177 |
| 3,030,373 | 4/1962 | Szlatinay | 548/177 |
| 3,031,073 | 4/1962 | Szlatinay | 548/177 |
| 3,818,025 | 6/1974 | Sugahara et al. | 548/177 |
| 4,192,804 | 3/1980 | Alicot et al. | 548/177 |
| 4,371,698 | 2/1983 | Alicot et al. | 548/177 |

FOREIGN PATENT DOCUMENTS

| | | | |
|---|---|---|---|
| 0015802 | 9/1980 | European Pat. Off. | 548/177 |
| 2135807 | 12/1972 | France | 548/176 |

OTHER PUBLICATIONS

K. Takiura, Chem. Abstracts 91:175331q, (1979), Purification of 2-mercaptobenzothiazole.

Primary Examiner—Donald G. Daus
Assistant Examiner—Mary E. Ceperley
Attorney, Agent, or Firm—Brooks, Haidt, Haffner & Delahunty

[57] ABSTRACT

A process for purifying crude synthetic mercaptobenzothiazole according to the invention, which comprises treating the crude mercaptobenzothiazole with aniline, filtering and washing the crystallized mercaptobenzothiazole with aniline and, if desired, recycling the liquid organic phases of the purification medium, wherein the crystallization of mercaptobenzothiazole, the filtration and the washing are carried out at a temperature of from 40° to 120° C.

9 Claims, No Drawings

PROCESS FOR THE PURIFICATION OF MERCAPTOBENZOTHIZAOLE

BACKGROUND OF THE INVENTION

The present invention relates to the purification of mercaptobenzothiazole, and more particularly, it relates to methods for purifying crude mercaptobenzothiazole obtained by synthetic processes.

2-Mercaptobenzothiazole is commercially utilized in the elastomer conversion as a vulcanization accelerator. Most importantly, it is a premier starting material for the synthesis of more complex vulcanization accelerators. These accelerators act both to delay the scorch time of the mixtures to be vulcanized and permit choosing the best vulcanization parameters for the preparation of a particular article. It is also employed for the synthesis of plant-protection or pharmaceutical compounds and is also included as an anti-corrosive agent in metal protection preparations.

Most of the known processes of manufacture, which are basically derived from U.S. Pat. No. 1,631,871, rely on the reaction of aniline, sulfur and carbon disulfide at high temperature and high pressure. Others rely either on the reaction of thiocarbanilide, carbon disulfide and sulfur (U.S. Pat. No. 1,712,968), or on the reaction of orthochloronitrobenzene, hydrogen sulfide or an alkali metal sulfide, and carbon disulfide (U.S. Pat. No. 1,960,205). Alternatively, German Pat. No. 2,551,060 uses the reaction of benzothiazole and sulfur.

The reaction products obtained from these various processes cannot be employed as such. The products so produced contain unreacted starting materials, for example, aniline, and they also contain by-products and intermediates such as benzothiazole and anilinobenzothiazole. Careful purification of the crude reaction products is required.

Numerous purification processes have been proposed so far and are the subject of U.S. Pat. Nos. 1,631,871; 2,090,233; 2,658,864; 2,730,528; 3,030,373; 3,031,073; and 3,818,025, and French Pat. Nos. 2,135,807 and 2,397,409. A discussion of these methods is at pages 2 to 4 of French Pat. No. 2,450,828 which discusses their respective disadvantages and suggests another purification technique which involves treating the crude synthesis product with aniline, the starting material of the reaction.

According to this technique, aniline can be added to the crude product either directly in the synthesis reactor, before release of the pressure to atmospheric pressure, at a temperature preferably in the range 180°–220° C., or, after release of the pressure to atmospheric pressure, at a temperature between ambient temperature and the boiling point of aniline, that is to say, in the range from 15° to 184° C. The mercaptobenzothiazole, so rendered insoluble in aniline, is filtered off after cooling to ambient temperature and is then washed with aniline. The aniline present in the filter cake can be removed, for example, by steam distillation or by vacuum evaporation. Because of the solubility of mercaptobenzothiazole in aniline, it is essential for an economical process that the organic phases originating from the filtration and the washing of the crystallized product be recycled.

The process of French Pat. No. 2,450,828 represents a very clear improvement relative to the prior art processes, because it makes it possible readily to recover the unreacted starting materials and the useable by-products which may be present in the reaction product (in particular, the benzothiazole). The recovery is facilitated because materials other than the starting materials for the reaction are used. This process virtually eliminates the problems posed by the treatment of aqueous wastes from conventional industrial plants.

However, the disadvantage of the process according to French Pat. No. 2,450,828 lies in the high aniline content which must be recovered from the product isolated at ambient temperature. Since this quantity is of the order of 40 to 50%, the unfavorable heat balance of this recovery severely compromises the advantages of the process.

THE INVENTION

It has now been found according to the present invention that the advantages of a purification process using aniline can be retained and its disadvantages can be eliminated. This derives from the discovery that, when mercaptobenzothiazole is crystallized in aniline, the crystallized compound obtained at ambient temperature or at a temperature in that neighborhood (15° to 30° C.) is not mercaptobenzothiazole itself, but an addition compound of mercaptobenzothiazole and aniline. This addition compound is stable at the temperatures mentioned. The interstitial aniline is readily removed by washing with water (also kept at 15° to 30° C.). In the resulting crystallized product (generally in the form of small cubes), it is found that an aniline content very close to the theoretical content (35.77%) is present in the mercaptobenzothiazole-aniline addition product.

Secondly, it is based on the discovery that when the temperature of the suspension obtained by crystallization of mercaptobenzothiazole in aniline is maintained at a value above 40° C., the crystals of the precipitated compound are generally needle-shaped. Filtration, at a temperature above 40° C., and washing with water, also maintained at a temperature above 40° C., produce a material virtually free of aniline and the properties of which are those of mercaptobenzothiazole.

Accordingly, the present invention provides a process for the purification of mercaptobenzothiazole comprising treatment of the crude product produced in the synthesis with aniline, and filtration and washing of the crystallized mercaptobenzothiazole with aniline. In certain embodiments, the liquid organic phases of the purification medium are recycled.

The present process is characterized in that the crystallization of the mercaptobenzothiazole, the filtration, and the washing are carried out at a temperature of from 40° to 120° C.

To carry out the purification of crude reaction mercaptobenzothiazole according to the invention, it is desirable to operate as follows:

1. Mixing of Aniline with the Reaction Product

The addition of aniline can be carried out directly in the synthesis reactor, preferably when the reaction is complete, before the pressure is reduced to atmospheric. The temperature is then between the reaction temperature and the solidification temperature of the crude product, that is, between 300° C. and 170° C., preferably between 220° C. and 180° C.

Alternatively, the process is carried out by adding aniline to the crude product obtained after the pressure is reduced to atmospheric, at a temperature between ambient temperature and the boiling point of aniline, that is, between 15° C. and 184° C., preferably between 45° C. and 120° C. According to the invention, the crude product can be added to aniline or the mixing can be carried out by simultaneous addition of both constituents.

2. Crystallization of Mercaptobenzothiazole

Whatever the temperature, within the ranges defined herein, at which the mixture of aniline and the crude reaction product is produced, crystallization of mercaptobenzothiazole takes place according to the invention at a temperature of between 40° and 120° C., and preferably between 45° and 80° C. in certain embodiments.

Thus, the crude product can be added to aniline so as to maintain a mixture temperature of 100° C. and then to cool it to 50° C. The addition can also be carried out so that the temperature of the mixture is 30° C., and the mixture is then heated to 50° C.

3. Filtration of Mercaptobenzothiazole

This is carried out in the temperature range chosen for crystallization, that is, from 40° C. to 120° C. In certain preferred embodiments, this is carried out at from 45° C. to 80° C.

4. Washing of Mercaptobenzothiazole

To remove the impurities, the filtered crystals are washed with aniline, which is also maintained at a temperature of between 40° and 120° C., preferably between 45° C. and 80° C.

5. Removal of Aniline

The crystals of purified mercaptobenzothiazole are next washed with water maintained at a temperature of from 40° C. to 120° C., and in certain embodiments, preferably from 45° C. to 80° C. Between 100° and 120° C., the water is used in the form of steam.

6. Drying of the Mercaptobenzothiazole

After washing with water, the crystals are dried by known means and then ground to produce the required particle size for the particular application.

The lower limit (40° C.) of the temperature range defined according to the present invention corresponds to the dissociation temperature of the mercaptobenzothiazole-aniline addition compound into its two components. The upper limit (120° C.) is selected so as to avoid dissolving too great a quantity of mercaptobenzothiazole in the organic phases obtained from the filtration and washing with aniline.

It is desirable for the economics of the process to recycle these phases. The recycling involves purging the impurities in the crystallization loop. By removing a selected volume of organic phase originating from the filtration of mercaptobenzothiazole, a quantity of impurities equal to that added by the reaction product is withdrawn from the crystallization loop.

This is based on recycling of the liquid organic phases a number of times without a purge during the time that steady-state operation is being achieved. In this way, as the impurity content becomes sufficiently high relative to that of mercaptobenzothiazole, losses of the latter product become economically acceptable. Aniline and benzothiazole can be recovered, in particular, from the purge. Not recycling the liquid phases or recycling them only partly would not, of course, constitute a departure from the scope of the invention.

The weight ratio of aniline to be employed in the first stage of the process according to the invention, either in the form of pure aniline or in the form of recycled liquid organic phase, can be varied from 2.5 to 6 times that of the crude mercaptobenzothiazole to be purified and is preferably between 3 and 4 times. The weight ratio of aniline to be employed for washing can vary from 0.4 to 1.2 times that of mercaptobenzothiazole considered as dry isolated product and is preferably between 0.5 and 0.8 times.

All parts, percentages, proportions and ratios herein are by weight, unless otherwise stated.

The following Example is given to illustrate embodiments of the invention as it is presently preferred to practice it. It will be understood that this Example is illustrative, and the invention is not to be considered as restricted thereto except as indicated in the appended claims.

EXAMPLE

This relates to the purification of the crude product produced by the reaction of sulfur, aniline and carbon disulfide, and describes the operating procedure after attainment of equilibrium during which the concentration of impurities in the organic phase resulting from the filtration has reached a sufficiently high level (35% in this Example).

Into an apparatus equipped with stirring and temperature measurement means, there is introduced 1000 g of recycled aniline originating from a previous process. Then, 300 g of crude reaction product to be purified, analyzing 87% mercaptobenzothiazole and taken from the outlet of the synthesis reactor after the pressure has been reduced to atmospheric, is added.

The mixing is carried out to maintain a temperature of 90° C. The solution obtained is then cooled to 50° C. and the resulting suspension is filtered in a temperature-controlled filter maintained at 50° C.

The product on the filter is washed with 150 g of aniline, added in three portions maintained at 50° C., and then with 1000 g of water, added in 200-gram portions and also maintained at 50° C. After draining and drying at 100° C., 255.5 g of mercaptobenzothiazole is obtained, analyzing 99% mercaptobenzothiazole with a melting point (uncorrected) of 178°–181° C.

The purification yield is 96.9% based on 100% mercaptobenzothiazole.

A selected quantity of organic phase equal to that entering the crystallization loop as the reaction product is removed from the aqueous phase of the filtrate derived from the filtration of the suspension of mercaptobenzothiazole to permit removal of impurities and is cooled to 20° C. The collected organic phases are combined and recycled to a further purification operation.

What is claimed is:

1. A process for the purification of crude synthetic mercaptobenzothiazole, which process comprises treating the crude mercaptobenzothiazole with aniline; crystallizing the aniline-treated mercaptobenzothiazole; filtering and recovering the crystallized materials; and washing the recovered crystals with aniline, wherein the crystallization, filtration, and washing of the mercaptobenzothiazole are carried out at a temperature of from 40° to 120° C.

2. A process according to claim 1 wherein the materials from the filtration and from the aniline wash are recycled to one step of the process.

3. A process according to claim 1 wherein the crude mercaptobenzothiazole is obtained from a reaction carried out at superatmospheric pressure and is mixed with aniline at a temperature of from 15° to 184° C. after the pressure has been reduced to atmospheric pressure, and the temperature of the mixture is thereafter brought to from 40° to 120° C.

4. A process according to claim 1 wherein the reaction producing crude mercaptobenzothiazole is carried out at superatmospheric pressure and the crude mercaptobenzothiazole is treated with aniline at the superatmospheric pressure at a temperature of from 170° to 300° C., reducing the pressure to atmospheric pressure, and cooling the mixture to a temperature of from 40° to 120° C.

5. A process according to claim 4 wherein the crude mercaptobenzothiazole is treated with aniline at a temperature of from 180° to 220° C. at superatmospheric pressure.

6. A process according to claim 1 wherein the aniline wash is followed by a water wash at a temperature of from 40° to 120° C.

7. A process according to claim 1 wherein the crystallization, filtration, and washing are carried out at a temperature of from 45° to 80°C.

8. A process according to claim 7 wherein the crystallization, filtration, and washing are carried out at a temperature of 50°C.

9. A process according to claim 1 wherein the mercaptobenzothiazole is obtained from the reaction of aniline, sulfur, and carbon disulfide.

* * * * *